US010036068B1

(12) United States Patent
Boutaud et al.

(10) Patent No.: US 10,036,068 B1
(45) Date of Patent: Jul. 31, 2018

(54) DIAGNOSIS, PROGNOSIS, AND TREATMENT OF MYOCARDIAL INFARCTION

(71) Applicant: Vanderbilt University, Nashville, TN (US)

(72) Inventors: Olivier Boutaud, Nashville, TN (US); Elias Haddad, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 72 days.

(21) Appl. No.: 13/937,011

(22) Filed: Jul. 8, 2013

Related U.S. Application Data (60) Provisional application No. 61/668,696, filed on Jul. 6, 2012.

(51) Int. Cl.
*C07H 21/02* (2006.01)
*C12Q 1/6883* (2018.01)
*A61K 31/4045* (2006.01)

(52) U.S. Cl.
CPC ........ *C12Q 1/6883* (2013.01); *A61K 31/4045* (2013.01)

(58) Field of Classification Search
None
See application file for complete search history.

(56) References Cited

U.S. PATENT DOCUMENTS 6,582,908 B2 * 6/2003 Fodor et al. ............... 506/9

OTHER PUBLICATIONS

SS174407330 for rs7541936, NCBI, NLM 2009.*
SS173724663 for rs4383756, NCBI, NLM, 2009.*
NEB catalog (1998/1999), pp. 121, 284.*
Kotani et al; Genomics, vol. 40, pp. 425-434, 1997.*
Ju et al; PNAS, vol. 92, pp. 4347-4351, 1995.*
Weksler, B.B., A.J. Marcus, and E.A. Jaffe, Synthesis of prostaglandin I2 (prostacyclin) by cultured human and bovine endothelial cells. Proc Natl Acad Sci U S A, 1977 . 74(9): p. 3922-6.
Marcus, A.J., et al., Synthesis of prostacyclin from platelet-derived endoperoxides by cultured human endothelial cells. J Clin Invest, 1980. 66(5): p. 979-86.
Czervionke, R.L., et al., Inhibition of prostacyclin by treatment of endothelium with aspirin. Correlation with platelet adherence. J Clin Invest, 1979. 63(5): p. 1089-92.
Charo, I.F., et al., Prostaglandin I2 is not a major metabolite of arachidonic acid in cultured endothelial cells from human foreskin microvessels. J Clin Invest, 1984. 74(3): p. 914-9.
Neri Serneri, G.G., et al., Physiologic role of coronary PGI2 and PGE2 in modulating coronary vascular response to sympathetic stimulation. Am Heart J, 1990. 119(4): p. 848-54.
Neri Serneri, G.G., et al., Defective coronary prostaglandin modulation in anginal patients. Am Heart J, 1990. 120(1): p. 12-21.
Gross, S., et al., Vascular wall-produced prostaglandin E2 exacerbates arterial thrombosis and atherothrombosis through platelet EP3 receptors. J Exp Med, 2007 . 204(2): p. 311-20.
Smith, J.P., Haddad, E.V., et al., PGE2 decreases reactivity of human platelets by activating EP2 and EP4. Thromb Res, 2010. 126(1): p. e23-9.
Fabre, J.E., et al., Activation of the murine EP3 receptor for PGE2 inhibits cAMP production and promotes platelet aggregation. Journal of Clinical Investigation, 2001. 107(5): p. 603-10.
Ma, H., et al., Increased bleeding tendency and decreased susceptibility to thromboembolism in mice lacking the prostaglandin E receptor subtype EP(3). Circulation, 2001. 104(10): p. 1176-80.
Fuster, V., et al., The pathogenesis of coronary artery disease and the acute coronary syndromes (1). New England Journal of Medicine, 1992. 326(4): p. 242-50.
Fuster, V., et al., The pathogenesis of coronary artery disease and the acute coronary syndromes (2). New England Journal of Medicine, 1992. 326(5): p. 310-8.
Kabbani, S.S., et al., Platelet reactivity characterized prospectively: a determinant of outcome 90 days after percutaneous coronary intervention. Circulation, 2001. 104(2): p. 181-6.
Kabbani, S.S., et al., Usefulness of platelet reactivity before percutaneous coronary intervention in determining cardiac risk one year later. American Journal of Cardiology, 2003. 91(7): p. 876-8.
Trip, M.D., et al., Platelet hyperreactivity and prognosis in survivors of myocardial infarction. New England Journal of Medicine, 1990. 322(22): p. 1549-54.
Huang, D.J., M.R. Nelson, and W. Holzgreve, Maldi-TOF mass spectrometry for trisomy detection. Methods in Molecular Biology, 2008. 444: p. 123-32.
Purcell, S., et al., PLINK: a tool set for whole-genome association and population-based linkage analyses. American Journal of Human Genetic, 2007. 81(3): p. 559-75.
American Heart Association. Heart Disease and Stroke Statistics—2005 Update. Dallas, Texas.
MacIntyre, D.E. and J.L. Gordon, Calcium-dependent stimulation of platelet aggregation by PGE. Nature, 1975. 258(5533): p. 337-9.
Bruno, J.J., L.A. Taylor, and M.J. Droller, Effects of prostaglandin E2 on human platelet adenyl cyclase and aggregation. Nature, 1974. 251(5477): p. 721-3.

(Continued)

*Primary Examiner* — Jehanne S Sitton
(74) *Attorney, Agent, or Firm* — Stites & Harbison PLLC; Mandy Wilson Decker (57) ABSTRACT

Methods are provided for diagnosis, prognosis, and treatment associated with a cardiovascular event in a subject as well as methods of providing anti-platelet therapy. The methods can comprise obtaining a sample from the subject, and determining the presence of at least two single nucleotide polymorphisms (SNP) in the sample selected from Rs7541936 in PTGER3, Rs977214 in PTGER3, and Rs2206343 in PTGER3. The methods can also comprise determining the presence in the sample of Rs4383756 in PTGER4. Some methods comprise administering conventional anti-platelet therapy to the subject if Rs4383756 in PTGER4 is present in the sample. Furthermore, some methods comprise administering an EP3 antagonist and/or conventional anti-platelet therapy to the subject if Rs4383756 in PTGER4 is not present in the sample. The cardiovascular event can involve thrombosis or an embolic event, a myocardial infarction, a stroke, a primary cardiovascular event, or coronary artery disease.

9 Claims, 5 Drawing Sheets

(56) References Cited

OTHER PUBLICATIONS

Vezza, R., et al., Prostaglandin E2 potentiates platelet aggregation by priming protein kinase C. Blood, 1993. 82(9): p. 2704-13.
Niccoli, G., et al. Myocardial No-Reflow in Humans. JACC, 2009. 54: p. 281-92.

* cited by examiner

DIAGNOSIS, PROGNOSIS, AND TREATMENT OF MYOCARDIAL INFARCTION

RELATED APPLICATIONS

This application claims priority from U.S. Provisional Application Ser. No. 61/668,696, filed Jul. 6, 2012, the entire disclosure of which is incorporated herein by this reference.

GOVERNMENT INTEREST

This invention was made with government support under Grant Number HL81009 awarded by the National Institutes of Health, Lung and Blood Institute, Specialized Centers of Clinically Oriented Research in Thrombosis Research. The government has certain rights in the invention.

TECHNICAL FIELD

The presently-disclosed subject matter relates to diagnosis, prognosis and treatment associated with a cardiovascular event. In particular, the presently-disclosed subject matter methods of providing anti-platelet therapy, and methods of diagnosis, prognosis, and treatment associated with a cardiovascular event, including myocardial infarction.

BACKGROUND

Cardiovascular disease remains the leading cause of death in the United States, accounting for over 40% of deaths and more than $394 billion in annual healthcare costs. Anti-platelet therapy is a cornerstone of acute and long-term management of cardiovascular disease, but current anti-platelet regimens do not reliably inhibit platelet activation in all patients leaving sub-groups of patients un-protected from recurrent cardiovascular events. Platelet hyperreactivity is associated with increased risk of coronary events and death from a cardiovascular cause. The risk of cardiac events following percutaneous coronary intervention (PCI) is 16.7% for patients with high baseline platelet reactivity compared to only 1.9% for patients with low platelet reactivity. After myocardial infarction, patients with high residual platelet reactivity have a relative risk of death of 5.9 compared to patients with normal or low platelet reactivity.

Platelet activation is a complex event mediated by a number of factors that are intrinsic and extrinsic to the platelet. Vascular injury stimulates platelet adhesion via activation of platelet glycoproteins. This is followed by platelet activation and by release of chemical mediators such as thrombin, ADP, thromboxane $A_2$, or epinephrine. These platelet activators have two main roles that include recruiting more platelets at the site of the wound and activating the platelets so that the platelets aggregate.

A the endothelium plays a role in the regulation of the platelet reactivity. Endothelial cells produce several factors that influence blood flow, blood coagulation and angiogenesis. These cells metabolize arachidonic acid to produce several prostaglandins, which play a role in the regulation of thrombus formation by modifying the platelet reactivity. Prostacyclin ($PGI_2$) inhibits platelet aggregation and attachment of platelets to the endothelial surface. In the microvasculature in humans, prostaglandin $E_2$ ($PGE_2$) is the major prostaglandin secreted by the endothelial cells. Indeed, in healthy humans both $PGI_2$ and $PGE_2$ play a physiologic role in modulating the coronary response to sympathetic stimulation and their defective production in patients with angina may be responsible for the paradoxical increase in coronary vascular resistance following sympathetic stimulation. However, the role of $PGE_2$ in the progression of atherosclerotic vascular disease and platelet function is not well-understood. In humans it has been observed that the effects of $PGE_2$ on platelet reactivity are not fully consistent, and can significantly differ among individuals in terms of platelet response.

Hence, there remains a need to determine the role of $PGE_2$ on platelet activity on a genetic level. There also remains a need to utilize such genetic information in the diagnosis, prognosis, and treatment associated with a cardiovascular event.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method for diagnosis, prognosis, and treatment associated with a cardiovascular event in a subject. In some embodiments the method comprises obtaining a sample from the subject and determining the presence of at least two single nucleotide polymorphisms (SNP) in the sample selected from Rs7541936 in PTGER3, Rs977214 in PTGER3, and Rs2206343 in PTGER3. In some embodiments the subject is identified as having an increased risk of a cardiovascular event if Rs7541936 in PTGER3 is present in the sample, if Rs977214 in PTGER3 is present in the sample, or if Rs2206343 in PTGER3 is present in the sample.

The cardiovascular event in the subject can be one of many known events, conditions, diseases or the like. Exemplary cardiovascular events include those involving thrombosis or an embolic event, a myocardial infarction (MI), a stroke, a primary cardiovascular event, coronary heart disease, or a combination thereof.

Furthermore, in some embodiments the method can further comprise determining the presence in the sample of Rs4383756 in PTGER4. In this regard, some exemplary methods further comprise recommending or administering an EP3 Antagonist to the subject if Rs4383756 in PTGER4 is not present in the sample. Other exemplary methods comprise further comprise recommending or administering conventional anti-platelet therapy to the subject. Still other exemplary methods further comprise recommending or administering conventional anti-platelet therapy to the subject if Rs4383756 in PTGER4 is present in the sample.

In some embodiments of the method, the subject has not had a primary cardiovascular event. In such embodiments, the method can further comprise determining the presence in the sample of Rs4383756 in PTGER4. Such embodiments can also further comprise conducting a platelet aggregation assay on the sample from the subject. Further still, in methods wherein the subject has not had a primary cardiovascular event, the methods can further comprise recommending or administering an EP3 Antagonist to the subject if Rs4383756 in PTGER4 is not present in the sample.

The presently-disclosed subject matter also includes a method of providing anti-platelet therapy. The method can comprise obtaining a sample from the subject, determining the presence of Rs4383756 in PTGER4 in the sample, and administering conventional anti-platelet therapy to the subject if Rs4383756 in PTGER4 is present in the sample, or administering an EP3 Antagonist, conventional anti-platelet therapy, or both to the subject if Rs4383756 in PTGER4 is not present in the sample. In some embodiments the subject has or has not had a primary cardiovascular event, has coronary heart disease, or has received percutaneous coronary intervention(s) (PCI). In some embodiments the EP3 Antagonist can be DG-041. Furthermore, in some embodiments the biological sample is selected from urine, serum, blood, plasma, saliva, sputum, feces, tear, hair, nails, and other samples including a cell from the subject.

Additionally, the presently-disclosed subject matter includes a kit for diagnosis, prognosis, and treatment associated with a cardiovascular event and/or anti-platelet therapy in a subject that comprises a probe for specifically determining the presence of at least two single nucleotide polymorphism (SNP) in a sample obtained from the subject, the SNPs being selected from Rs7541936 in PTGER3, Rs977214 in PTGER3, Rs2206343 in PTGER3, and Rs4383756 in PTGER4. In some embodiments the kit comprises a probe for specifically determining the presence of at least one SNP in a sample obtained from the subject selected from Rs7541936 in PTGER3, Rs977214 in PTGER3, and Rs2206343 in PTGER3, as well as a probe for specifically determining the presence of Rs4383756 in PTGER4.

In some embodiments the kit can comprise a probe for specifically determining the presence of at least three SNPs in a sample obtained from the subject, selected from Rs7541936 in PTGER3, Rs977214 in PTGER3, Rs2206343 in PTGER3, and Rs4383756 in PTGER4. In some embodiments the kit can comprise a probe for specifically determining the presence of each of the following SNPs in a sample obtained from the subject: Rs7541936 in PTGER3, Rs977214 in PTGER3, Rs2206343 in PTGER3, and Rs4383756 in PTGER4. In yet further embodiments the probe can detect the presence of each of Rs7541936 in PTGER3, Rs977214 in PTGER3, and Rs2206343 in PTGER3.

In some embodiments the kit can further comprise an EP3 receptor antagonist. IN specific embodiments the EP3 receptor antagonist can be DG-041. Furthermore, in some embodiments the kits can further comprise an apparatus that is capable of identifying a SNP in a sample, including the SNPs described herein. Similarly, in some embodiments of the methods described herein, the methods can further comprise a step of providing an apparatus that is capable of identifying a SNP in a sample.

Further features and advantages of the present invention will become evident to those of ordinary skill in the art after a study of the present application.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotides and polypeptides identified herein include sequence and other information in the GEN-BANK®/GENPEPT® database, which sequence and other information is expressly incorporated by reference. Unless otherwise indicated or apparent, the references to the GEN-BANK®/GENPEPT® database are references to the most recent version of the database as of the filing date of this Application.

While the terms used herein are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes methods and kits for use in diagnosing, prognosticating, and treating myocardial infarction, and methods and kits for use in providing anti-platelet therapy.

In contrast to the potentiation effect on platelet aggregation that is most often reported, nanomolar concentrations of PGE$_2$ inhibit platelet aggregation induced by the thromboxane receptor agonist U46,619, as well as by an agonist of the thrombin receptor subtype 4 (PAR4-AP) in approximately 26% of individuals (responders). In approximately 31% of individuals, PGE$_2$ affected the timing but not the final magnitude of aggregation (partial responders), and in the remaining approximately 42%, PGE$_2$ did not have detectable effects (nonresponders). While these percentages are based on a specific study, those of ordinary skill will recognize that these results indicate that individuals can be phenotypically categorized as responders or nonresponders, and, optionally, also as partial responders.

The present inventors discovered that prevention by PGE$_2$ of thromboxane-induced platelet aggregation in a quarter of the population is EP4-dependent. In the rest of the population, pharmacological antagonism of EP3 leads to PGE$_2$ having an EP4-dependent inhibitory effect similar to PGE$_2$ responders. Without being bound by theory or mechanism, it was determined that the PGE$_2$-responsive phenotypes depend on a by a balance between the EP3 and EP4 receptor subtypes, where EP3 determines the non-responder phenotype and EP4 determines the responder phenotype. In other words, the human platelet EP3 receptor can induce a pro-aggregatory effect and the EP4 receptor can be responsible for the inhibitory effect on platelet aggregation. It was also observed that an antagonist of the EP3 receptor shifts the phenotypes from non-responder to responder, thereby identifying the EP3 receptor as a target for pharmacologic inhibition of platelet aggregation (e.g., DG041; DeCode Genetics, Reykjavik, Iceland). The present inventors identified relevant polymorphisms in the EP3 and EP4 receptor genes.

In this regard, methods of the presently-disclosed subject matter include determining the presence of one or more single nucleotide polymorphisms (SNP) in a biological sample obtained from a subject. The SNPs can include one or more of the following: Rs7541936 in PTGER3, Rs977214 in PTGER3, Rs2206343 in PTGER3, and Rs4383756 in PTGER4. In some embodiments the SNP include two or more of the following: Rs7541936 in PTGER3, Rs977214 in PTGER3, Rs2206343 in PTGER3, and Rs4383756 in PTGER4.

Risk assessment using genetic testing for disease susceptibility is a useful approach to possible prevention or attenuation of disease severity, which has implications for patient survival and quality of life, as well as in the context of economic costs to patients and to society. Thus, the presently-disclosed subject matter further includes methods that include interventions and/or changes in therapeutic strategy with a view towards prevention of future disease in subjects predisposed to cardiovascular events, e.g., myocardial infarction.

As will be recognized by those of ordinary skill in the art upon study of the present application, identification of the Rs7541936 in PTGER3, Rs977214 in PTGER3, Rs2206343 in PTGER3, and/or Rs4383756 in PTGER4 SNPs in a biological sample obtained from the subject in accordance with the presently-disclosed subject matter can be accomplished in a variety of ways. For example, in some embodiments, DNA could be isolated from a blood sample from a subject, and amplification of DNA sequences flanking the polymorphic region of the SNP variant can be performed, e.g., using commercially-available SNP genotyping technologies.

The terms "diagnosing" and "diagnosis" as used herein refer to methods by which the skilled artisan can estimate and even determine whether or not a subject is suffering from a given disease or condition. Along with diagnosis, clinical "prognosis" or "prognosticating" is also an area of great concern and interest. It is important to know the relative risk associated with particular conditions in order to plan the most effective therapy. If an accurate prognosis can be made, appropriate therapy, and in some instances less severe therapy or more effective therapy, for the patient can be chosen. In some embodiments of the presently disclosed subject matter, a method includes identifying a subject as having an increased risk of a cardiovascular event (e.g., condition involving arterial thrombosis or embolic events, e.g., myocardial infarction (MI) or stroke) if one or more of Rs7541936 in PTGER3, Rs977214 in PTGER3, and Rs2206343 the SNPs in PTGER3 are present in the sample. In some embodiments, the subject is identified has having an increased risk of MI if Rs7541936 in PTGER3 is present in the sample. In some embodiments, the subject is identified has having an increased risk if Rs977214 in PTGER3 is present in the sample. In some embodiments, the subject is identified has having an increased risk if Rs2206343 in PTGER3 is present in the sample.

In this regard, making a prognosis or "prognosticating" can refer to predicting a clinical outcome (with or without medical treatment), selecting an appropriate treatment (or whether treatment would be effective), or monitoring a current treatment and potentially changing the treatment, based on the presence of a mutation in the PTGER3 gene and/or PTGER4 gene. "Prognosticating" as used herein refers to methods by which the skilled artisan can predict the course or outcome of a condition in a subject. The term "prognosis" can refer to the ability to predict the course or outcome of a condition with up to 100% accuracy, or predict that a given course or outcome is more or less likely to occur. The term "prognosis" can also refer to an increased probability that a certain course or outcome will occur; that is, that a course or outcome is more likely to occur in a subject exhibiting a mutation in the gene, when compared to those individuals not exhibiting the mutation in the gene. In certain embodiments, a prognosis is about a 5% chance of a given expected outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an outcome can be performed using statistical analysis. Statistical significance is often determined by comparing two or more populations, and determining a confidence interval and/or a p value. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

As used herein, the term "subject" includes both human and animal subjects. The preferred subject is a human. The subject can be male or female. The subject can be of any age. In some embodiments, the subject is an adult (i.e., 18 years or older). In some embodiments, the subject is a child (i.e., younger than 18 years).

As used herein, the term "biological sample" refers to a sample from the subject including a cell, for example, urine, serum, blood, plasma, saliva, sputum, feces, tear, hair, nails, and other samples including a cell from the subject.

The presently-disclosed subject matter contemplates identifying the presence of a mutation in DNA of the PTGER3 gene and/or the PTGER4 gene, or by detecting a product of a mutated PTGER3 gene and/or the PTGER4 gene, wherein the gene product can be a protein or a nucleotide. For example, one skilled in the art would recognize upon study of the present application that the presently-disclosed subject matter includes a nucleotide bases mutation(s) in the PTGER3 gene and/or the PTGER4 gene, as well as a mutation(s) in an mRNA or a polypeptide resulting from such gene mutation, relative to the mRNA and the polypeptide that would result from a wild-type PTGER3 gene and/or the PTGER4 gene. As such, determining the presence of a mutation of the presently-disclosed subject matter in a PTGER3 gene and/or PTGER4 gene is inclusive of identifying an amino acid substitution in the polypeptide product of the PTGER3 gene and/or the PTGER4 gene, etc.

In accordance with the presently-disclosed subject matter, the presence of a mutation in the PTGER3 gene and/or the PTGER4 gene can be determined using various techniques known to those of ordinary skill in the art. An exemplary methodology for identifying a mutation makes use of probes, e.g., probes that can selectively bind a nucleotide or polypeptide including the mutation. For another example, polymerase chain reaction (PCR) techniques can be used.

In some embodiments of the presently-disclosed subject matter, a method for diagnosis, prognosis, and treatment associated with myocardial infarction (MI) in a subject includes obtaining a sample from the subject; and determining the presence of one or more SNPs in the sample selected from: Rs7541936 in PTGER3, Rs977214 in PTGER3, and Rs2206343 in PTGER3. In some embodiments, the subject is identified has having an increased risk of MI if one, two, or three of the SNPs in PTGER3 are present in the sample. In some embodiments, the subject is identified has having an increased risk of MI if Rs7541936 in PTGER3 is present in the sample. In some embodiments, the subject is identified has having an increased risk of MI if Rs977214 in PTGER3 is present in the sample. In some embodiments, the subject is identified has having an increased risk of MI if Rs2206343 in PTGER3 is present in the sample.

In some embodiments, the subject has not had a primary cardiovascular event. In some embodiments, the subject has had a primary cardiovascular event, and the method can be performed to provide an indication of risk of another such event, e.g., myocardial infarction. In some embodiments, the subject has coronary artery disease.

In some embodiments, in addition to determining the presence in a sample of a SNP in PTGER3, methods can include determining the presence in the sample of Rs4383756 in PTGER4. When PTGER4 is present in the sample, the subject can be identified as one who is not likely to benefit from treatment with an EP3 receptor antagonist. In such cases, the subject may benefit from conventional therapy, e.g., conventional anti-platelet therapy. When PTGER4 is not present in the sample, the subject can be identified as one who can benefit from EP3 receptor antagonist. As such, an EP3 receptor antagonist can be recommended, administered, and/or provided to the subject if PTGER4 is not present in the sample. In some embodiments, the EP3 receptor antagonist treatment can be provided together with conventional therapy, e.g., conventional anti-platelet therapy.

In some embodiments, in addition to determining the presence in a sample of a SNP in PTGER3, methods can include conducting a platelet aggregation assay on the sample, as described by Smith et al., Thromb Res, 2010. The platelet aggregation assay can be used to identify the subject as one who is or who is not likely to benefit from treatment with an EP3 receptor antagonist. When the subject is identified as one who is not likely to benefit from treatment with an EP3 receptor antagonist, the subject may benefit from conventional therapy, e.g., conventional anti-platelet therapy. When the subject is identified as one who can benefit from EP3 receptor antagonist treatment, an EP3 receptor antagonist can be recommended, administered, and/or provided to the subject. In some embodiments, the EP3 receptor antagonist treatment can be provided together with conventional therapy, e.g., conventional anti-platelet therapy.

The presently-disclosed subject matter further includes methods for providing anti-platelet therapy or for determining whether EP3 receptor antagonist treatment may be beneficial (e.g., provide a clinical benefit), which include determining the presence of Rs4383756 in PTGER4 in a sample obtained from a subject. In some embodiments, the subject has not had a primary cardiovascular event. In some embodiments, the subject has had a primary cardiovascular event. In some embodiments, the subject has coronary artery disease. In some embodiments, the subject has received percutaneous coronary interventions (PCI).

When Rs4383756 in PTGER4 is present in the sample, the subject can be identified as one who is not likely to benefit from treatment with an EP3 receptor antagonist. In such cases, the subject may benefit from conventional therapy, e.g., conventional anti-platelet therapy. When Rs4383756 in PTGER4 is not present in the sample, the subject can be identified as one who can benefit from EP3 receptor antagonist. As such, an EP3 receptor antagonist can be recommended, administered, and/or provided to the subject if Rs4383756 in PTGER4 is not present in the sample. In some embodiments, the EP3 receptor antagonist treatment can be provided together with conventional therapy, e.g., conventional anti-platelet therapy.

In some embodiments, when Rs4383756 in PTGER4 is not present in the sample, a clinical benefit associated with administrating an EP3 receptor antagonist is predicted. Exemplary EP3 receptor antagonists can include DG-041 (DeCode Genetics, Reykjavik, Iceland). In some embodiments, when Rs4383756 in PTGER4 is present in the sample, a clinical benefit associated with administrating an EP4 receptor antagonist is not predicted.

In some embodiments of the presently-disclosed subject matter, a method includes determining whether a subject has had a primary cardiovascular event. In some embodiments, if the subject has had a primary cardiovascular event, the method further includes determining the presence of a Rs4383756 in PTGER4. Where the SNP in PTGER4 is not present in the sample, the method can further include recommending, administering, and/or providing an EP3 receptor antagonist to the subject, or identifying the subject as being responsive to EP3 receptor antagonist treatment. Convention treatment can also be provided in some cases. Where the SNP in PTGER4 is present in the sample, the EP3 receptor antagonist treatment would generally not be recommended, but conventional treatment could be provided in some cases.

In some embodiments, if the subject has not had a primary cardiovascular event, the risk of such an event can be determined by determining the presence of one or more SNPs in a sample obtained from the subject, selected from Rs7541936 in PTGER3, Rs977214 in PTGER3, and Rs2206343 in PTGER3, as described herein above. In some embodiments, the subject has initially been determined to have an increased risk or a cardiovascular event using conventional risk factors. In some embodiments, only those subject that have been initially determined to have intermediate to high risk (or greater than low risk) of a cardiovascular event are selected for further screening for the presence of a SNP in PTGER3. For subject who have not had a primary cardiovascular event, and in some embodiments for those subjects who have been identified as having an increased risk of a cardiovascular event (e.g., MI), further screening can be conducted to determine whether EP3 receptor antagonist treatment can be beneficial. In such embodiments, the method includes determining the presence of Rs4383756 in PTGER4 in a sample obtained from the subject. Where the SNP in PTGER4 is not present in the sample, the subject can be identified as one for which EP3 receptor antagonist treatment can be beneficial.

The presently-disclosed subject matter further includes systems and kits, which are useful for practicing embodiments of the methods as described herein. In some embodiments, a kit is provided including reagents for practicing the methods and disclosed herein. In some embodiments, the kit can include a probe or primer pair for use in selectively identifying the mutation(s) in the PTGER3 gene and/or the PTGER4 gene. In some embodiments, a kit or system is provided including an apparatus capable of identifying a mutation in the PTGER3 gene and/or the PTGER4 gene in a biological sample from the subject.

In some embodiments a kit is provided including a probe (probe or primer pair) for specifically determining the presence of one, two, three, or four single nucleotide polymorphism (SNP) in a sample, selected from: Rs7541936 in PTGER3, Rs977214 in PTGER3, Rs2206343 in PTGER3, and Rs4383756 in PTGER4.

In some embodiments, the kit further includes an EP3 receptor antagonist. In some embodiments, the EP3 receptor antagonist is DG-041.

The presently-disclosed subject matter is further illustrated by the following specific but non-limiting examples. Some of the following examples are prophetic, notwithstanding the numerical values, results and/or data referred to and contained in the examples. Additionally, the following examples may include compilations of data that are representative of data gathered at various times during the course of development and experimentation related to the present invention.

EXAMPLES

Example 1

This Examples describes a study conducted to characterize the regulation of thromboxane-dependent human platelet activation by $PGE_2$, and particularly nanomolar concentrations of $PGE_2$. Platelets were collected from individuals and studied by light transmission aggregometry. Next, it was observed how low nanomolar concentrations of $PGE_2$ effect aggregation and dense granule release induced by sub-maximal concentrations of an agonist of the thromboxane receptor (U46,619), thrombin, collagen, and ADP.

Figure 1:
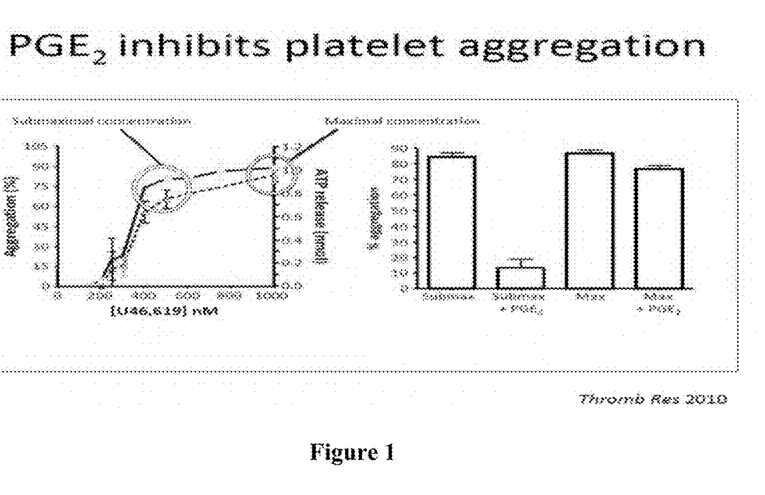
FIG. 1 includes a plot showing platelet aggregation as a function of concentration of thromboxane receptor agonist U46,619 (left), and a plot showing platelet aggregation for samples exposed to sub-maximal (submax) and maximal (max) concentrations of U46,619 both in the presence and absence of $PGE_2$ (right).

It was observed that healthy volunteers demonstrated significant interindividual variation in platelet response to $PGE_2$. In all volunteers, a selective EP2 agonist inhibited U46,619-induced aggregation, and a selective EP3 agonist potentiated aggregation induced by a sub-threshold concentration of U46,619. At concentrations of agonists producing full activation of the platelets (max), $PGE_2$ did not affect either aggregation or granule release, even when micromolar concentrations of $PGE_2$ were used (FIG. 1).

Figure 2:
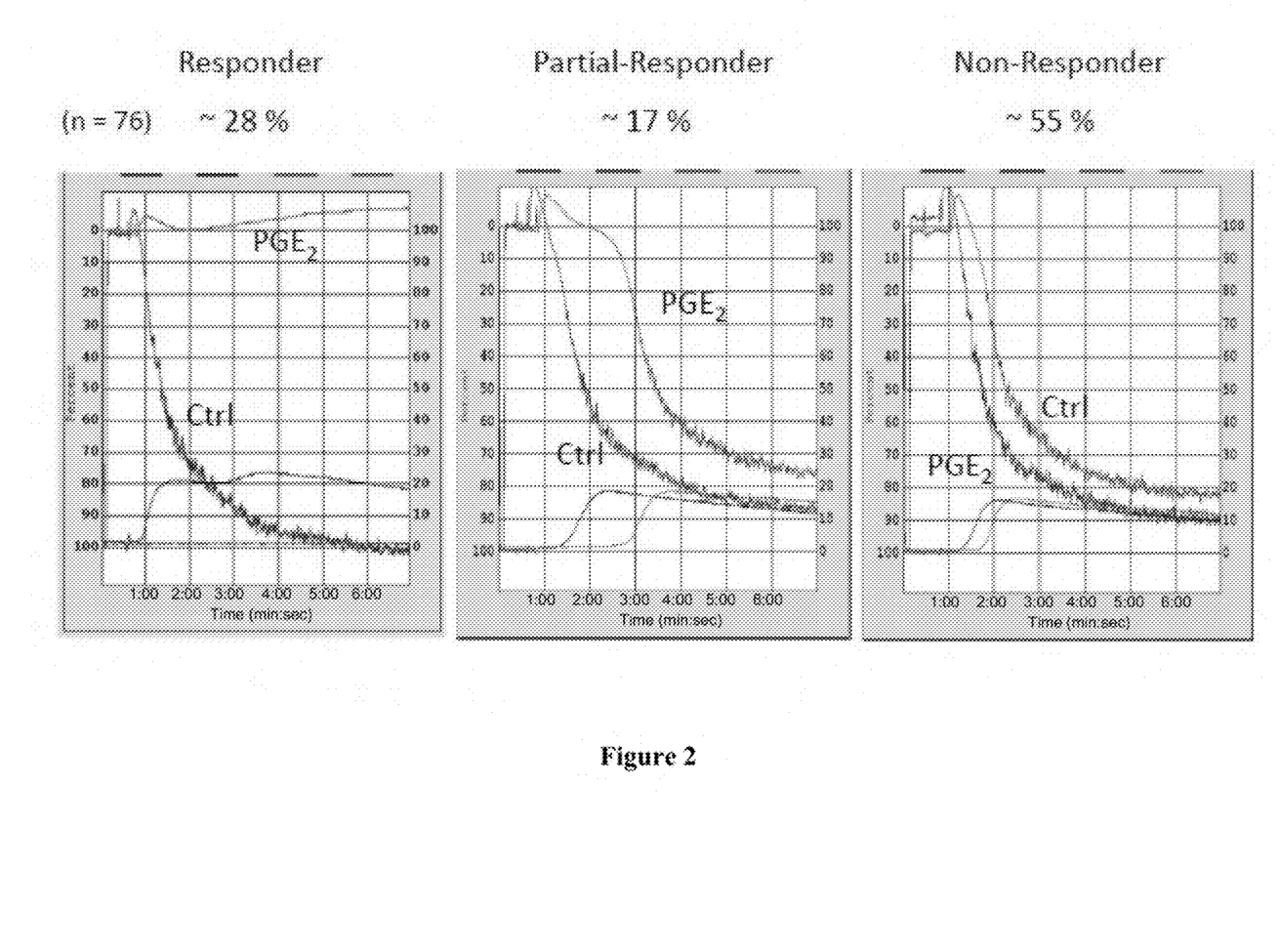
FIG. 2 includes plots showing percent of platelet activity inhibition for control samples and samples exposed to $PGE_2$, and showing that individuals can be categorized as responder, partial-responder, or non-responder based on how platelet activity responds to $PGE_2$.
Figure 3:
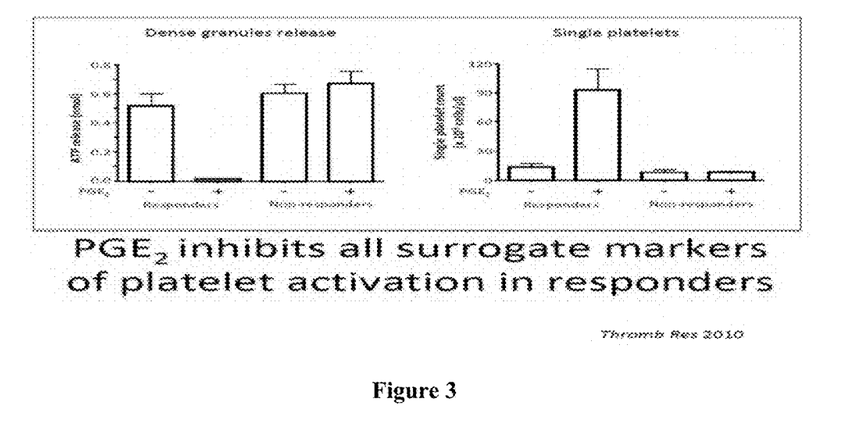
FIG. 3 includes plots showing ATP release (left—dense granules release) and single platelet count (right—single platelets) for responder and non-responder samples both in the absence (−) and presence (+) of $PGE_2$.

The interindividual variation was also noted by observing seventy-six (76) individuals. Specifically, it was found that approximately 28% of individuals display a strong inhibition of platelet activity in response to $PGE_2$, some are partial responders (17%), and an important subset does not show significant inhibition of platelet aggregation in response to $PGE_2$ (55% non-responders) (FIG. 2). Subsequently, it was observed $PGE_2$ at nanomolar concentrations was capable of preventing aggregation and dense granule release induced by sub-maximal concentrations of U46, 619 and thrombin in responder populations, but not in non-responder populations (FIG. 3).

Figure 4:
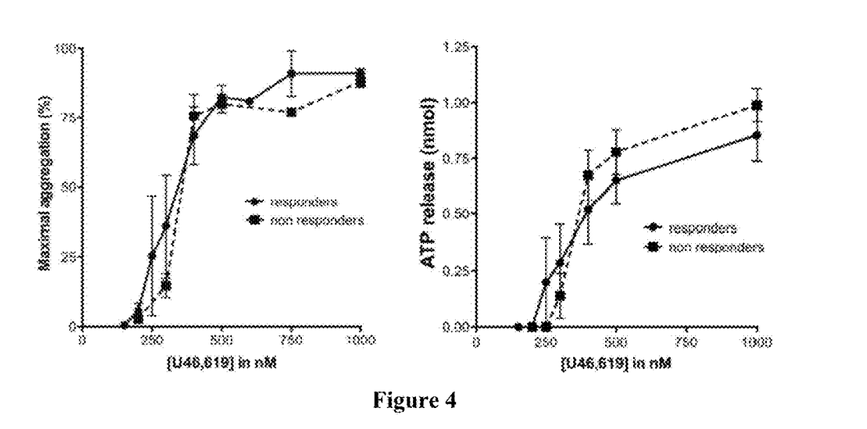
FIG. 4 includes plots of maximal aggregation (left) and ATP release (right) as a function of U46,610 concentration for both responder and non-responder individuals, and showing that there is little to no difference in U46,619 dose-response between the different phenotypic groups.
Figure 5:
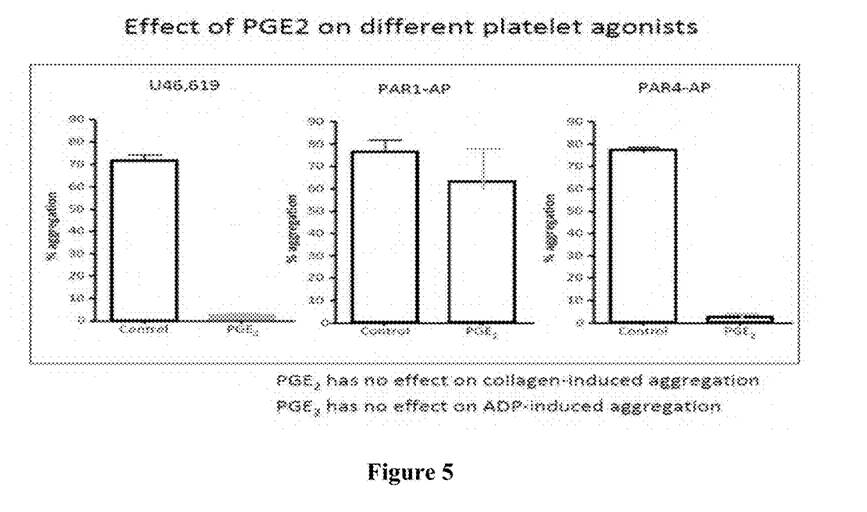
FIG. 5 includes plots showing aggregation for control samples and samples that are exposed to $PGE_2$ in the presence of U46,619, protease-activated receptor (PAR) 1 activating peptide (PAR1-AP), and PAR4-AP.

Samples from responders and non-responders were also exposed to different doses of U46,619. No significant no difference in U46,619 dose-response was observed between the different phenotypic groups (FIG. 4). It was further observed that $PGE_2$ had no effect on collagen-induced or ADP-induced aggregation, but of course did have an effect on U46,610 aggregation (FIG. 5).

These results cumulatively demonstrate that $PGE_2$ plays a role in the regulation of platelet reactivity. These results also demonstrate that there is a phenotypic variation among healthy subjects in the response seen to $PGE_2$.

Example 2

This Example describes procedure conducted to characterize the effects that EP3 and EP4 have on the inhibitory effects of $PGE_2$. Furthermore, after identifying the EP3 and EP4 receptors as potential locations for these phenotypes, this Example describes polymorphisms equating to the phenotypes were identified in the PTGER3 and PTGER4 genes.

Figure 6:
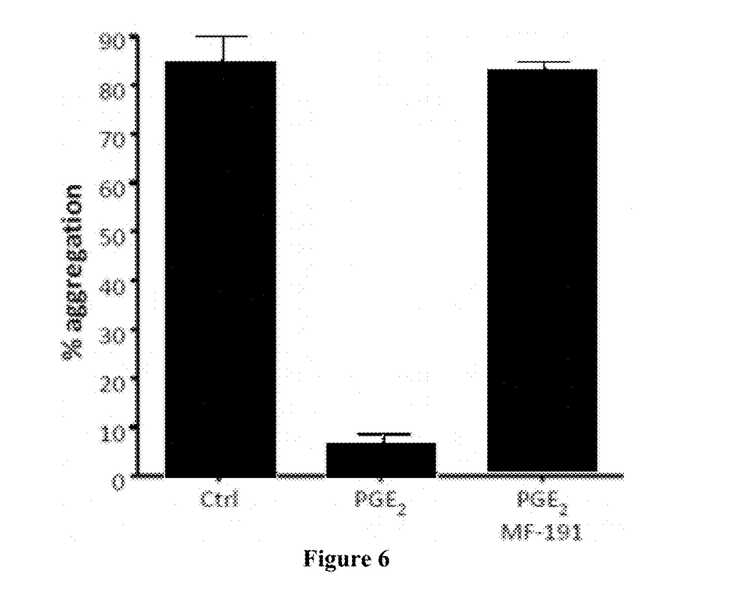
FIG. 6 includes a plot showing aggregation stimulated with a submaximal dose of U46,619 for responder phenotype samples that were under control conditions, exposed to 100 nM $PGE_2$, or exposed to MF-191, an EP4 antagonist, before addition of 100 nM $PGE_2$.
Figure 7:
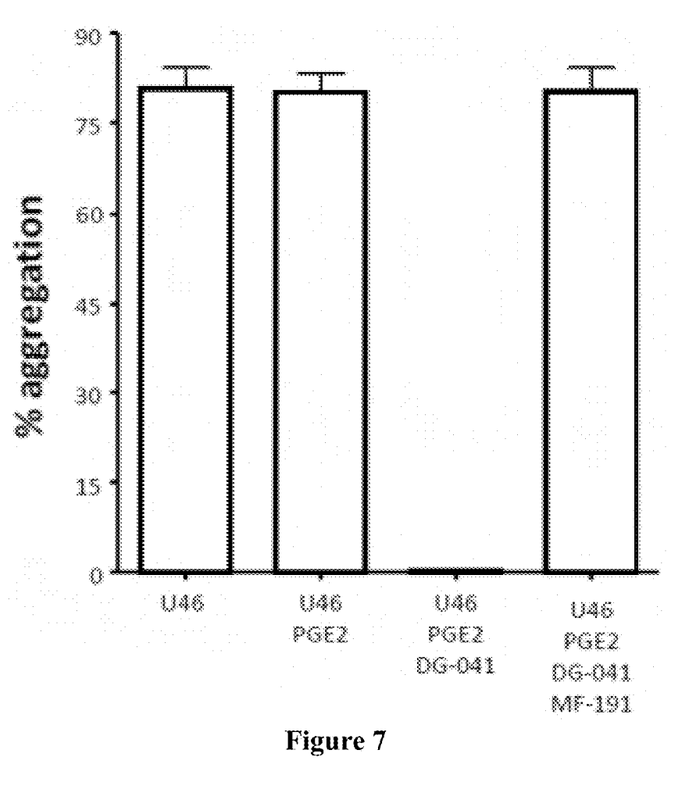
FIG. 7 includes a plot showing aggregation for samples exposed to a) U46,691, b) U46,691 and $PGE_2$, c) U46,691, $PGE_2$, and DG-041, and d) U46,691, $PGE_2$, DG-041, and MF-191.

As shown in FIG. 6, for individuals having the responder phenotype, the inhibitory effect of 100 nM of $PGE_2$ was abolished by an antagonist of EP4, MF-191 (Merck-Frosst, Montreal, Canada). Furthermore, the selective EP3 antagonist DG-041 converted all $PGE_2$ nonresponders to full responders (FIG. 7). Because platelet reactivity correlates with cardiovascular risk, the data suggest that EP3 antagonists may reduce risk for thrombotic cardiovascular events in non-responding individual. Thus, both EP3 and EP4 were identified as having roles in the interindividual variation of platelet response to $PGE_2$.

Following these results, polymorphisms in the PTGER3 gene were analyzed. The analysis showed that genetic polymorphisms in the PTGER3 gene (EP3 receptor) correlated with an acute myocardial infarction (MI) clinical phenotype compared to a control group of patients with stable CAD and no prior history of MI. The polymorphisms included Rs7541936, Rs977214, and Rs2206343 in PTGER3.

A gender effect was observed such that men with a history of ST-elevation myocardial infarction (STEMI) have an odds ratio (OR) of 2.4 (p=0.012) and 2.3 (p=0.032) for the presence of two single nucleotide polymorphisms (SNPs) with p values of 0.012 and 0.032, respectively (Table 1). Analyzing the data for both genders for the three identified SNPs shows odds ratios of 1.7, 1.8 and 1.2 with p values of 0.030, 0.039 and 0.04 respectively. Thus, these results indicated the potential for a new paradigm in antiplatelet therapy by targeting the EP3 receptor with an antagonist such as DG-041 (DeCode Genetics, Reykjavik, Iceland).

TABLE 1

Odds Ratios for different Risk Factors in Men.

| Risk factor | Adjusted odds ratio | 95% CI |
|---|---|---|
| CRP | 1.45 | 1.25-1.68 |
| Total cholesterol | 2.35 | 2.03-2.74 |
| EP3 Polymorphism | 2.3 | 1.07-4.98 |
|  | 2.4 | 1.20-4.76 |
| Current smoking | 1.87 | 1.62-2.16 |
| Systolic blood pressure | 1.50 | 1.30-1.73 |

Subsequently, analysis of 32 non-responding subjects and 12 responding subjects identified SNP Rs4383756 in PTGER4 as being associated with the responsive phenotype, having an odds ratio of about 3.3 and p-value of 0.02. Thus, the fact that a subjects lacked the Rs4383756 in PTGER4 SNP can suggest that the subject is a non-responder.

Throughout this document, various publications, patents, and patent applications are mentioned. All such references are herein incorporated by reference, including the references set forth in the following list:

REFERENCES

1. Weksler, B. B., A. J. Marcus, and E. A. Jaffe, *Synthesis of prostaglandin I2 (prostacyclin) by cultured human and bovine endothelial cells.* Proc Natl Acad Sci USA, 1977. 74(9): p. 3922-6.
2. Marcus, A. J., et al., *Synthesis of prostacyclin from platelet-derived endoperoxides by cultured human endothelial cells.* J Clin Invest, 1980. 66(5): p. 979-86.
3. Czervionke, R. L., et al., *Inhibition of prostacyclin by treatment of endothelium with aspirin. Correlation with platelet adherence.* J Clin Invest, 1979. 63(5): p. 1089-92.
4. Charo, I. F., et al., *Prostaglandin I2 is not a major metabolite of arachidonic acid in cultured endothelial cells from human foreskin microvessels.* J Clin Invest, 1984. 74(3): p. 914-9.
5. Neri Serneri, G. G., et al., *Physiologic role of coronary PGI2 and PGE2 in modulating coronary vascular response to sympathetic stimulation.* Am Heart J, 1990. 119(4): p. 848-54.
6. Neri Serneri, G. G., et al., *Defective coronary prostaglandin modulation in anginal patients.* Am Heart J, 1990. 120(1): p. 12-21.
7. Gross, S., et al., *Vascular wall-produced prostaglandin E2 exacerbates arterial thrombosis and atherothrombosis through platelet EP3 receptors.* J Exp Med, 2007. 204(2): p. 311-20.
8. Smith, J. P., Haddad, E. V., et al., *PGE2 decreases reactivity of human platelets by activating EP2 and EP4.* Thromb Res, 2010. 126(1): p. e23-9.
9. Fabre, J. E., et al., *Activation of the murine EP3 receptor for PGE2 inhibits cAMP production and promotes platelet aggregation.* Journal of Clinical Investigation, 2001. 107(5): p. 603-10.
10. Ma, H., et al., *Increased bleeding tendency and decreased susceptibility to thromboembolism in mice lacking the prostaglandin E receptor subtype EP(3).* Circulation, 2001. 104(10): p. 1176-80.
11. Fuster, V., et al., *The pathogenesis of coronary artery disease and the acute coronary syndromes (1).* New England Journal of Medicine, 1992. 326(4): p. 242-50.
12. Fuster, V., et al., *The pathogenesis of coronary artery disease and the acute coronary syndromes (2).* New England Journal of Medicine, 1992. 326(5): p. 310-8.
13. Kabbani, S. S., et al., *Platelet reactivity characterized prospectively: a determinant of outcome 90 days after percutaneous coronary intervention.* Circulation, 2001. 104(2): p. 181-6.
14. Kabbani, S. S., et al., *Usefulness of platelet reactivity before percutaneous coronary intervention in determining cardiac risk one year later.* American Journal of Cardiology, 2003. 91(7): p. 876-8.
15. Trip, M. D., et al., *Platelet hyperreactivity and prognosis in survivors of myocardial infarction.* New England Journal of Medicine, 1990. 322(22): p. 1549-54.
16. Huang, D. J., M. R. Nelson, and W. Holzgreve, *Maldi-TOF mass spectrometry for trisomy detection.* Methods in Molecular Biology, 2008. 444: p. 123-32.
17. Purcell, S., et al., *PLINK: a tool set for whole-genome association and population-based linkage analyses.* American Journal of Human Genetic, 2007. 81(3): p. 559-75.
18. American Heart Association. Heart Disease and Stroke Statistics—2005 Update. Dallas, Tex.
19. MacIntyre, D. E. and J. L. Gordon, *Calcium-dependent stimulation of platelet aggregation by PGE.* Nature, 1975. 258(5533): p. 337-9.
20. Bruno, J. J., L. A. Taylor, and M. J. Droller, *Effects of prostaglandin E2 on human platelet adenyl cyclase and aggregation.* Nature, 1974. 251(5477): p. 721-3.
21. Vezza, R., et al., *Prostaglandin E2 potentiates platelet aggregation by priming protein kinase C.* Blood, 1993. 82(9): p. 2704-13.
22. Niccoli, G., et al. *Myocardial No-Reflow in Humans.* JACC, 2009. 54: p. 281-92.

What is claimed is:

1. A kit for diagnosis, prognosis, and treatment associated with a cardiovascular event and/or anti-platelet therapy in a subject, comprising:
   a set of two, three, or four single nucleotide polymorphism (SNP)-specific probes wherein each SNP-specific probe is selected from the group consisting of:
      a probe for detecting Rs7541936 in PTGER3 in a sample obtained from the subject;
      a probe for detecting Rs977214 in PTGER3 in a sample obtained from the subject;
      a probe for detecting Rs2206343 in PTGER3 in a sample obtained from the subject; and
      a probe for detecting Rs4383756 in PTGER4 in a sample obtained from the subject;
   the kit including the probe for detecting Rs4383756 in PTGER4 in the set of probes and/or an EP3 receptor antagonist;
   wherein the kit does not include any probes in addition to the set of probes; and
   wherein the probes are fluorescently-labeled.

2. The kit of claim 1, comprising: the SNP-specific probe for detecting Rs4383756 in PTGER4 in a sample obtained from the subject.

3. The kit of claim 1, comprising a set of SNP-specific probes consisting of three or four probes selected from the group consisting of:
   a probe for detecting Rs7541936 in PTGER3 in a sample obtained from the subject;
   a probe for detecting Rs977214 in PTGER3 in a sample obtained from the subject,
   a probe for detecting Rs2206343 in PTGER3 in a sample obtained from the subject; and
   a probe for detecting Rs4383756 in PTGER4 in a sample obtained from the subject.

4. The kit of claim 1, comprising a set of SNP-specific probes consisting of:
   a probe for detecting Rs7541936 in PTGER3 in a sample obtained from the subject;
   a probe for detecting Rs977214 in PTGER3 in a sample obtained from the subject,
   a probe for detecting Rs2206343 in PTGER3 in a sample obtained from the subject; and
   a probe for detecting Rs4383756 in PTGER4 in a sample obtained from the subject.

5. The kit of claim 1, comprising an EP3 receptor antagonist.

6. The kit of claim 5, wherein the EP3 receptor antagonist is DG-041.

7. The kit of claim 1, comprising a set of SNP-specific probes consisting of:
   a probe for detecting Rs7541936 in PTGER3 in a sample obtained from the subject;
   a probe for detecting Rs977214 in PTGER3 in a sample obtained from the subject; and
   a probe for detecting Rs2206343 in PTGER3 in a sample obtained from the subject.

8. The kit of claim 1, and further comprising an apparatus capable of identifying a SNP in the sample.

9. The kit of claim 1, wherein each probe is a single nucleic acid molecule.

* * * * *